US010534052B2

(12) United States Patent
Jiang et al.

(10) Patent No.: US 10,534,052 B2
(45) Date of Patent: Jan. 14, 2020

(54) FMRI BIOMARKER OF NEURODEGENERATIVE DISEASE

(71) Applicant: GEORGETOWN UNIVERSITY, Washington, DC (US)

(72) Inventors: Xiong Jiang, Falls Church, VA (US); Maximilian Riesenhuber, Vienna, VA (US)

(73) Assignee: Georgetown University, Washington, DC (US)

( * ) Notice: Subject to any disclaimer, the term of this patent is extended or adjusted under 35 U.S.C. 154(b) by 1108 days.

(21) Appl. No.: 14/774,750

(22) PCT Filed: Mar. 14, 2014

(86) PCT No.: PCT/US2014/027442
§ 371 (c)(1),
(2) Date: Sep. 11, 2015

(87) PCT Pub. No.: WO2014/152529
PCT Pub. Date: Sep. 25, 2014

(65) Prior Publication Data
US 2016/0025828 A1 Jan. 28, 2016

Related U.S. Application Data

(60) Provisional application No. 61/784,402, filed on Mar. 14, 2013.

(51) Int. Cl.
G01R 33/48 (2006.01)
A61B 5/055 (2006.01)
A61B 5/00 (2006.01)

(52) U.S. Cl.
CPC ........ *G01R 33/4806* (2013.01); *A61B 5/0042* (2013.01); *A61B 5/055* (2013.01);
(Continued)

(58) Field of Classification Search
CPC . A61B 5/055; A61B 2576/026; A61B 5/0042; A61B 5/4088; A61B 5/4839; G01R 33/4806
See application file for complete search history.

(56) References Cited

U.S. PATENT DOCUMENTS

2005/0085705 A1* 4/2005 Rao .................. A61B 5/055
600/345
2012/0197105 A1* 8/2012 Mezer ................ A61B 5/055
600/410

OTHER PUBLICATIONS

Fox et al., "Using Serial Registered Brain Magnetic Resonance Imaging to Measure Disease Progression in Alzheimer Disease," Mar. 2000, American Medical Association, Arch Neurol/vol. 57, pp. 339-344.*

(Continued)

*Primary Examiner* — Angela M Hoffa
(74) *Attorney, Agent, or Firm* — Kilpatrick Townsend & Stockton LLP

(57) ABSTRACT

Provided herein are methods related to identifying an early, asymptomatic (prodromal) stage of a neurodegenerative disease or identifying a subject with a symptomatic neurodegenerative disease, including, for example, mild cognitive impairment (MCI), Alzheimer's Disease (AD), or HIV-associated neurocognitive disorder (HAND), using functional MRI data from the subject. Methods are also provided for treating a subject identified with the methods taught herein and for modifying or selecting treatment based on the results of fMRI. Methods are also available for staging neurodegenerative disease and for identifying agents useful in treating them.

20 Claims, 4 Drawing Sheets

(52) U.S. Cl.
CPC .......... *A61B 5/4088* (2013.01); *A61B 5/4839* (2013.01); *A61B 2576/026* (2013.01)

(56) References Cited

OTHER PUBLICATIONS

Liu et al., "Regional homogeneity, functional connectivity and imaging markers of Alzheimer's disease: A review of resting-state fMRI studies," 2008, Neuropsychologia 46, pp. 1649-1656.*
Wu et al. "Normal aging decreases regional homogeneity of the motor areas in the resting state." Neuroscience Letters 423 (2007) 189-193. (Year: 2007).*
He et al. "Regional coherence changes in the early stages of Alzheimer's disease: A combined structural and resting-state functional MRI study." NeuroImage 35 (2007) 488-500. (Year: 2007).*
Zang et al. "Regional homoheneity approach to fMRI data analysis." NeuroImage 22 (2004) 394-400. (Year: 2004).*
Adolphs et al., Abnormal processing of social information from faces in autism, Journal of Cognitive Neuroscience, vol. 13, 2001, pp. 232-240.
Adolphs et al., A mechanism for impaired fear recognition after amygdala damage, Nature, vol. 433, 2005, pp. 68-72.
Aguirre et al., The inferential impact of global signal covariates in functional neuroimaging analyses, Neuroimage, vol. 8, 1998, pp. 302-306.
Bair et al., Correlated firing in macaque visual area MT: time scales and relationship to behaviour, Journal of Neuroscience, vol. 21, 2001, pp. 1676-1697.
Baron-Cohen et al., The autism-spectrum quotient (AQ): evidence from Asperger syndrome/high-functioning autism, males and females, scientists and mathematicians, Journal of Autism and Developmental Disorders, vol. 31, 2001, pp. 5-17.
Barton et al., Are patients with social developmental disorders prosopagnosic? Perceptual heterogeneity in the Asperger and socioemotional processing disorders, Brain, vol. 127, 2004, pp. 1706-1716.
Blanz, A morphable model for the synthesis of 3D faces, Proceedings of the 26th annual conference on Computer graphics and interactive techniques, 1999, pp. 187-194.
Bölte et al., Facial affect recognition training in autism: can we animate the fusiform gyrus?, Behavioral Neuroscience, vol. 120, 2006, pp. 211-216.
Bookheimer et al., Frontal contributions to face processing differences in autism: evidence from fMRI of inverted face processing, Journal of International Neuropsychological Society, vol. 14, 2008, pp. 922-932.
Brett et al., Region of interest analysis using an SPM toolbox, CD-ROM in NeuroImage, vol. 16, No. 2, Jun. 2-6, 2002, 1 page.
Buracas et al., Efficient design of event-related fMRI experiments using M-sequences, NeuroImage, vol. 16, Issue 3, Part A, Jul. 2002, pp. 801-813.
Casanova et al., Minicolumnar abnormalities in autism, Acta Neuropathologica, vol. 112, Sep. 2006, pp. 287-303.
CBS News Staff, Aricept study shows benefits for moderate, severe Alzheimer's patients, Healthpop. CBS/AP, Web Accessed Feb. 10, 2016 at <https://web.archive.org/web/20120309080826/http://www.cbsnews.com/8301-504763_162-57393588-10391704/aricept-study-shows-benefits-for-moderate-severe-alzheimers-patients/>, Mar. 8, 2012.
Conturo et al., Neuronal fiber pathway abnormalities in autism: an initial MRI diffusion tensor tracking study of hippocampo-fusiform and amygdalo-fusiform pathways, Journal of International Neuropsychological Society, vol. 14, Issue 6, Nov. 2008, pp. 933-946.
Critchley et al., The functional neuroanatomy of social behaviour: changes in cerebral blood flow when people with autistic disorder process facial expressions, Brain, vol. 123, Part 11, Nov. 2000, pp. 2203-2212.

Dawson et al., Neurocognitive and electrophysiological evidence of altered face processing in parents of children with autism: implications for a model of abnormal development of social brain circuitry in autism, Development and Psychopathology, vol. 17, Issue 3, 2005, pp. 679-697.
Degutis et al., Functional plasticity in ventral temporal cortex following cognitive rehabilitation of a congenital prosopagnosic, Journal of Cognitive Neuroscience, vol. 19, No. 11, Nov. 2007, pp, 1790-1802.
Deshpande et al., Integrated local correlation: a new measure of local coherence in fMRI data, Human Brain Mapping, vol. 30, Issue 1, Jan. 2009, pp. 13-23.
Diamond et al., Why faces are and are not special: an effect of expertise, Journal of Experimental Psychology. General, vol. 115, Issue 2, Jun. 1986, pp. 107-117.
Dorrn et al., Developmental sensory experience balances cortical excitation and inhibition, Nature, vol. 465, Jun. 17, 2010, pp. 932-936.
Eden et al., Evidence for a relationship between the heterogeneity of local regional correlations within the VWFA and reading ability, Poster presented at Annual Meeting of the Society for Neuroscience, Washington, DC., 2011, 2 pages.
Epstein et al., A cortical representation of the local visual environment, Nature, vol. 392, Apr. 9, 1998, pp. 598-601.
Fang et al., Duration-dependent fMRI adaptation and distributed viewer-centered face representation in human visual cortex, Cerebral Cortex, vol. 17, Issue 6, Jun. 2007, pp. 1402-1411.
Freedman et al., Experience-dependent sharpening of visual shape selectivity in inferior temporal cortex, Cerebral Cortex, vol. 16, Issue 11, Nov. 2006, pp. 1631-1644.
Friston et al., Characterizing evoked hemodynamics with fMRI, NeuroImage, vol. 2, Jun. 1995, pp. 157-165.
Geschwind, Advances in autism, Annual Review of Medicine, vol. 60, 2009, pp. 367-380.
Gilaie-Dotan et al., Sub-exemplar shape tuning in human face-related areas, Cerebral Cortex, vol. 17, Issue 2, Feb. 2007, pp. 325-338.
Goh et al., Reduced neural selectivity increases fMRI adaptation with age during face discrimination, NeuroImage, vol. 51, Issue 1, May 15, 2010, pp. 336-344.
Golarai et al., Differential development of high-level visual cortex correlates with category-specific recognition memory, Nature Neuroscience, vol. 10, Issue 4, Apr. 2007, pp. 512-522.
Grady et al., Effect of task difficulty on cerebral blood flow during perceptual matching of faces, Human Brain Mapping, vol. 4, Issue 4, 1996, pp. 227-239.
Grelotti et al., fMRI activation of the fusiform gyrus and amygdala to cartoon characters but not to faces in a boy with autism, Neuropsychologia, vol. 43, Issue 3, 2005, pp. 373-385.
Grill-Spector et al., Repetition and the brain: neural models of stimulus-specific effects, Trends in Cognitive Sciences, vol. 10, Issue 1, Jan. 2006, pp. 14-23.
Grill-Spector et al., The fusiform face area subserves face perception, not generic within-category identification, Nature Neuroscience, vol. 7, Issue 5, May 2004, pp. 555-562.
Hadjikhani et al., Abnormal activation of the social brain during face perception in autism, Human Brain Mapping, vol. 28, Issue 5, May 2007, pp. 441-449.
Haxby et al., The distributed human neural system for face perception, Trends in Cognitive Sciences, vol. 4, Issue 6, Jun. 2000, pp. 223-233.
Haxby et al., The effect of face inversion on activity in human neural systems for face and object perception, Neuron, vol. 22, Issue 1, Jan. 1999, pp. 189-199.
Healy et al., New Alzheimer's pill more likely to cause misery, medical experts say, Los Angeles Times. Los Angeles Times, Accessed Feb. 10, 2016, at <http://articles.latimes.com/2012/mar/22/health/la-he-aricept-fda-20120323>, Mar. 22, 2012.
Hedley et al., Face recognition performance of individuals with Asperger syndrome on the Cambridge Face Memory Test, Autism Research, vol. 4, Issue 6, Dec. 2011, pp. 449-455.

(56) References Cited

OTHER PUBLICATIONS

Howard et al., The heterogeneity of local regional correlation in hippocampus and caudate predicts behavioural performance in old adults, Society of Neuroscience, 2011, Abstract 2 pages.

Hubl et al., Functional imbalance of visual pathways indicates alternative face processing strategies in autism, Neurology, vol. 61, Issue 9, Nov. 2003, pp. 1232-1237.

Humphreys et al., Cortical patterns of category-selective activation for faces, places and objects in adults with autism, Autism Research, vol. 1, Issue 1, Feb. 2008, pp. 52-63.

International Application No. PCT/US2014/027442, International Preliminary Report on Patentability dated Sep. 24, 2015, 5 pages.

International Application No. PCT/US2014/027442, Written Opinion dated Jul. 17, 2014, 3 pages.

Jermakowicz et al., Relationship Between Spontaneous and Evoked Spike-Time Correlations in Primate Visual Cortex, Journal of Neurophysiology, vol. 101, Issue 5, May 2009, pp. 2279-2289.

Jiang et al., A novel technique to estimate neuronal selectivity using fMRI, Program No. 619.08. 2011 Neuroscience Meeting Planner. Washington, DC: Society for Neuroscience, 2011, 2 pages.

Jiang et al., A quantitative link between face discrimination deficits and neuronal selectivity for faces in autism, Neuroimage: Clinical, vol. 2, Feb. 26, 2013, pp. 320-331.

Jiang et al., Categorization training results in shape- and category-selective human neural plasticity, Neuron, vol. 53, Issue 6, Mar. 15, 2007, pp. 891-903.

Jiang et al., Evaluation of a shape-based model of human face discrimination using fMRI and behavioral techniques, Neuron, vol. 50, Issue 1, Apr. 6, 2006, pp. 159-172.

Kanwisher et al., The fusiform face area: a cortical region specialized for the perception of faces, Philosophical Transactions of the Royal Society of London, Series B, Biological Sciences, vol. 361, Issue 1476, Dec. 29, 2006, pp. 2109-2128.

Kanwisher et al., The fusiform face area: a module in human extrastriate cortex specialized for face perception, Journal of Neuroscience, vol. 17, Issue 11, Jun. 1, 1997, pp. 4302-4311.

Kleinhans et al., Abnormal functional connectivity in autism spectrum disorders during face processing, Brain, vol. 131, Part 4, Apr. 2008, pp. 1000-1012.

Klin et al., A normed study of face recognition in autism and related disorders, Journal of Autism and Developmental Disorders, vol. 29, Issue 6, Dec. 1999, pp. 499-508.

Kobatake et al., Effects of shape-discrimination training on the selectivity of inferotemporal cells in adult monkeys, Journal of Neurophysiology, vol. 80, Issue 1, Jul. 1998, pp. 324-330.

Kourtzi et al., Representation of the perceived 3-D object shape in the human lateral occipital complex, Cerebral Cortex, vol. 13, Issue 9, Sep. 2003, pp. 911-920.

Mahon et al., Action-related properties shape object representations in the ventral stream, Neuron, vol. 55, Issue 3, Aug. 2, 2007, pp. 507-520.

Miller et al., Activity of neurons in anterior inferior temporal cortex during a short-term memory task, Journal of Neuroscience, vol. 13, Issue 4, Apr. 1993, pp. 1460-1478.

Murray et al., Attention increases neural selectivity in the human lateral occipital complex, Nature Neuroscience, vol. 7, Issue 1, Jan. 2004, pp. 70-74.

Paakki et al., Alterations in regional homogeneity of resting-state brain activity in autism spectrum disorders, Brain Research, vol. 1321, Mar. 19, 2010, pp. 169-179.

Perlman et al., Experimental manipulation of face-evoked activity in the fusiform gyrus of individuals with autism, Social Neuroscience, vol. 6, Issue 1, Feb. 2011, pp. 22-30.

Pierce et al., Face processing occurs outside the fusiform 'face area' in autism: evidence from functional MRI, Brain, vol. 124, Part 10, Oct. 2001, pp. 2059-2073.

Pierce et al., The brain response to personally familiar faces in autism: findings of fusiform activity and beyond, Brain, vol. 127, Part 12, Dec. 2004, pp. 2703-2716.

Riesenhuber et al., Appearance isn't everything: news on object representation in cortex, Neuron, vol. 55, Issue 3, Aug. 2007, pp. 341-344.

Riesenhuber et al., Neural mechanisms of object recognition, Current Opinion in Neurobiology, vol. 12, Issue 2, Apr. 2002, pp. 162-168.

Rubenstein et al., Model of autism: increased ratio of excitation/inhibition in key neural systems, Brain, and Behavior, vol. 2, Issue 5, Oct. 2003, pp. 255-267.

Riesenhuber et al., Task effects, performance levels, features, configurations, and holistic face processing: a reply to Rossion, Acta Psychologica, vol. 132, Issue 3, Nov. 2009, pp. 286-292.

Scherf et al., Location, Location, Location: Alterations in the Functional Topography of Face—but not Object—or Place-Related Cortex in Adolescents with Autism, Frontiers in Human Neuroscience, vol. 4, Article 26, Mar. 22, 2010, 16 pages.

Schultz et al., Abnormal ventral temporal cortical activity during face discrimination among individuals with autism and Asperger syndrome, Archives of General Psychiatry, vol. 57, Issue 4, Apr. 2000, pp. 331-340.

Schultz et al., Developmental deficits in social perception in autism: the role of the amygdala and fusiform face area, International Journal of Developmental Neuroscience, vol. 23, Issue 2-3, Apr.-May 2005, pp. 125-141.

Seitz et al., A common framework for perceptual learning, Current Opinion in Neurobiology, vol. 17, Issue 2, Apr. 2007, pp. 148-153.

Shukla et al., Regional homogeneity of fMRI time series in autism spectrum disorders, Neuroscience Letters, vol. 476, Issue 1, May 26, 2010, pp. 46-51.

Snow et al., Impaired visual scanning and memory for faces in high-functioning autism spectrum disorders: it's not just the eyes, Journal of International Neuropsychological Society, vol. 17, Issue 6, Nov. 2011, pp. 1021-1029.

Sunaert et al., Attention to speed of motion, speed discrimination, and task difficulty: an fMRI study, NeuroImage, vol. 11, Issue 6 Part 1, Jun. 2000, pp. 612-623.

Weeks et al., The salience of facial expression for autistic children, Journal of Child Psychology and Psychiatry, vol. 28, Issue 1, Jan. 1987, pp. 137-151.

Weigelt et al., Face Recognition Deficits in Autism Spectrum Disorders Are Both Domain Specific and Process Specific, Neuroscience and Biobehavioral Reviews, vol. 36, 2012, pp. 1060-1084.

Wörgötter et al., A detailed model of the primary visual pathway in the cat: comparison of afferent excitatory and intracortical inhibitory connection schemes for orientation selectivity, Journal of Neuroscience, vol. 11, Issue 7, Jul. 1991, pp. 1959-1979.

Yovel et al., The neural basis of the behavioral face-inversion effect, Current Biology, vol. 15, Issue 24, Dec. 20, 2005, pp. 2256-2262.

Zang et al., Regional homogeneity approach to fMRI data analysis, NeuroImage, vol. 22, Issue 1, May 2004, pp. 394-400.

\* cited by examiner

FMRI BIOMARKER OF NEURODEGENERATIVE DISEASE

This application claims the benefit of U.S. Application No. 61/784,402, filed on Mar. 14, 2013, which is hereby incorporated in its entirety by this reference.

STATEMENT REGARDING FEDERALLY FUNDED RESEARCH

This invention was made with government support under grant number R01AG036863 awarded by the National Institutes of Health. The government has certain rights in the invention.

BACKGROUND

Neurodegenerative disease, like Alzheimer's disease (AD) and mild cognitive impairment (MCI), are a public health problem of enormous proportions. It is estimated that 5.4 million people currently suffer from AD in the United States. This figure is likely underestimated due to the high number of undiagnosed patients in the community. By the year 2050, AD is projected to affect 16 million people. The annual cost in the United States of AD alone is approximately $200 billion.

SUMMARY

Provided herein are methods of identifying a subject with an early, asymptomatic stage of a neurodegenerative disease or a subject with a symptomatic (more advanced) stage of a neurodegenerative disease. The methods comprise selecting a subject in need of screening for the early, asymptomatic stage or the symptomatic stage of a neurodegenerative disease; placing the subject in a magnetic resonance imaging (MRI) machine; acquiring functional MRI (fMRI) data from the subject, optionally, while the subject performs an activation task; and calculating a measure of local regional heterogeneity ($H_{corr}$) in one or more brain regions. $H_{corr}$ is calculated using a computer readable medium including program instructions for calculating $H_{corr}$. An decrease in $H_{corr}$ as compared to $H_{corr}$ from a control subject is indicative of a subject with an early, asymptomatic stage of a neurodegenerative disease, whereas an increase in $H_{corr}$ as compared to $H_{corr}$ from a control subject is indicative of a subject with a symptomatic neurodegenerative disease. Optionally the neurodegenerative disease is mild cognitive impairment (MCI), Alzheimer's Disease (AD), or HIV-associated neurocognitive disorder. Optionally, the one or more brain regions include the hippocampus. Optionally, the method of claim 1, further comprising repeating the steps of placing the subject in an MRI, acquiring a fMRI, and calculating the $H_{corr}$ one or more times so as to assess the trend in $H_{corr}$ changes in the subject. An accelerated rate of change rate of change in $H_{corr}$ in the subject as compared to a control indicates an early, asymptomatic stage of the neurodegenerative disease.

Further provided are methods of treating a subject with an early, asymptomatic stage of a neurodegenerative disease or a subject with a symptomatic neurodegenerative disease comprising identifying a subject with an early, asymptomatic stage of a neurodegenerative disease or a symptomatic neurodegenerative disease using fMRI and $H_{corr}$ as taught herein administering to the subject an effective amount of an agent that prevents or delays the onset of symptoms of the neurodegenerative disease. Optionally, the method further comprises assessing the level of $H_{corr}$ after administering the agent to the subject and/or selecting a drug that changes $H_{corr}$ in the subject toward or within control values or stabilizes the $H_{corr}$ of the subject over time.

Also provided is a method of staging a neurodegenerative disease comprising selecting a subject with a neurodegenerative disease; placing the subject in an MRI machine; acquiring fMRI data from the subject, optionally, while the subject performs an activation task, calculating a measure of local regional heterogeneity ($H_{corr}$); calculating a measure of local regional heterogeneity ($H_{corr}$) in one or more brain regions, wherein $H_{corr}$ is calculated using a computer readable medium including program instructions for calculating $H_{corr}$; comparing the $H_{corr}$ from the subject to a plurality of $H_{corr}$ values corresponding to subjects with different stages of the neurodegenerative; and staging the neurodegenerative disease in the subject by identifying one or differences between the $H_{corr}$ from the subject and the plurality of $H_{corr}$ values corresponding to subjects with different stages of the neurodegenerative disease.

A method of determining the effectiveness of a treatment for a neurodegenerative disease is also provided that includes the steps of selecting a subject with a neurodegenerative disease; placing the subject in an MRI machine; acquiring fMRI data from the subject, optionally, while the subject performs an activation task; calculating a measure of local regional heterogeneity ($H_{corr}$) in one or more brain regions, wherein $H_{corr}$ is calculated using a computer readable medium including program instructions for calculating $H_{corr}$; and comparing the $H_{corr}$ as calculated to the $H_{corr}$ of the subject prior to administration of an agent. A change in the $H_{corr}$ after treatment toward a control $H_{corr}$ indicates the agent is effective in treating the neurodegenerative disease. No change in $H_{corr}$ or a modulation in $H_{corr}$ away from control values indicates the agent is ineffective in treating the neurodegenerative disease in the subject.

DESCRIPTION OF DRAWINGS

FIG. 2), but not effective in subjects at early stages of the disease (low $H_{corr}$).

DETAILED DESCRIPTION

Figure 1:
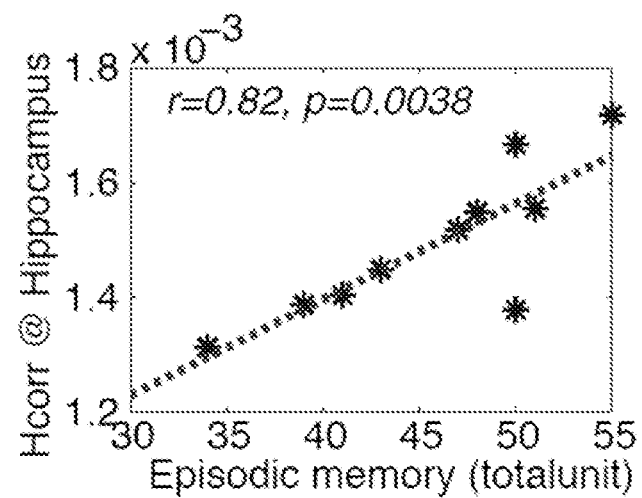
FIG. 1 shows that $H_{corr}$ in the hippocampus, panel A) can predict episodic memory performance in healthy older adults. Higher $H_{corr}$ correlates with a better performance in healthy adults, signifying more selective neural activation patterns.

Provided herein are methods of identifying a subject with an early, asymptomatic (prodromal) stage of a neurodegenerative disease or a subject with a symptomatic (more advanced) stage of a neurodegenerative disease. The methods comprise selecting a subject in need of screening for the early, asymptomatic stage or the symptomatic stage of a neurodegenerative disease; placing the subject in an MRI machine; acquiring functional MRI (fMRI) data from the subject, optionally, while the subject performs an activation task or while the subject is at rest; and calculating a measure of local regional heterogeneity ($H_{corr}$) in one or more brain regions. $H_{corr}$ is calculated using a computer readable medium including program instructions for calculating $H_{corr}$. A decrease in $H_{corr}$ as compared to $H_{corr}$ from a control subject (or a control group) is indicative of a subject with an early, asymptomatic stage of a neurodegenerative disease, whereas an increase in $H_{corr}$ as compared to $H_{corr}$ from a control subject is indicative of a subject with a symptomatic neurodegenerative disease. Optionally the neurodegenerative disease is mild cognitive impairment (MCI), Alzheimer's Disease (AD), or HIV-associated neurocognitive disorder. Optionally, the one or more brain regions include the hippocampus. Optionally, the method of claim 1, further comprising repeating the steps of placing the subject in an MRI, acquiring a fMRI, and calculating the $H_{corr}$ one or more times so as to assess the trend in $H_{corr}$ changes in the subject. An accelerated rate of change rate of change in $H_{corr}$ in the subject as compared to a control indicates an early, asymptomatic stage of the neurodegenerative disease.

As used throughout, an increase or decrease or a rate of change in a trend of decreasing or increasing $H_{corr}$ levels can be a 10, 20, 30, 40, 50, 60, 70, 80, 90, or 100% change, or any amount in between as compared to control. In some cases, the difference between a subject with an early, asymptomatic stage of a neurodegenerative disease and a healthy control or the difference between a subject with a symptomatic neurodegenerative disease and a healthy subject can be marked by difference of one to two standard deviations or more. Similarly, an accelerated rate of change in a rate of decreasing $H_{corr}$ in a subject with an early, asymptomatic neurodegenerative disease can different from a healthy control by one to two standards deviations or more.

A neurodegenerative disease is often marked by subtle cellular changes that precede the symptomatic period. Thus, the period of subtle cellular changes is often overlooked. It is only once the subject begins to experience symptoms, such as motor or memory impairment, that the subject is currently diagnosed. For example, the reliable detection of pre-symptomatic and prodromal Alzheimer's disease (AD) is a major challenge. The present disclosure shows one of earliest changes indicating AD is the modulation in neuronal specificity, which, without being limited by theory, is probably due to synaptic toxicity caused by Aβ formations. These modulations can be detected using $H_{corr}$, an fMRI analysis measure developed to probe neuronal specificity as sparseness of neuronal activations. Briefly, $H_{corr}$ estimates neuronal specificity as the variance of local voxel-wise correlations in a predefined brain region. $H_{corr}$ is a highly sensitive and robust measure of neuronal specificity that can be quantitatively linked to cognitive performance and impairments. Another unique and significant advantage of $H_{corr}$ is that it can be calculated for any functional or anatomical brain region from a single data set, thus making it an ideal tool to investigate AD, which is often associated with widespread pathological changes in the brain.

Figure 2:
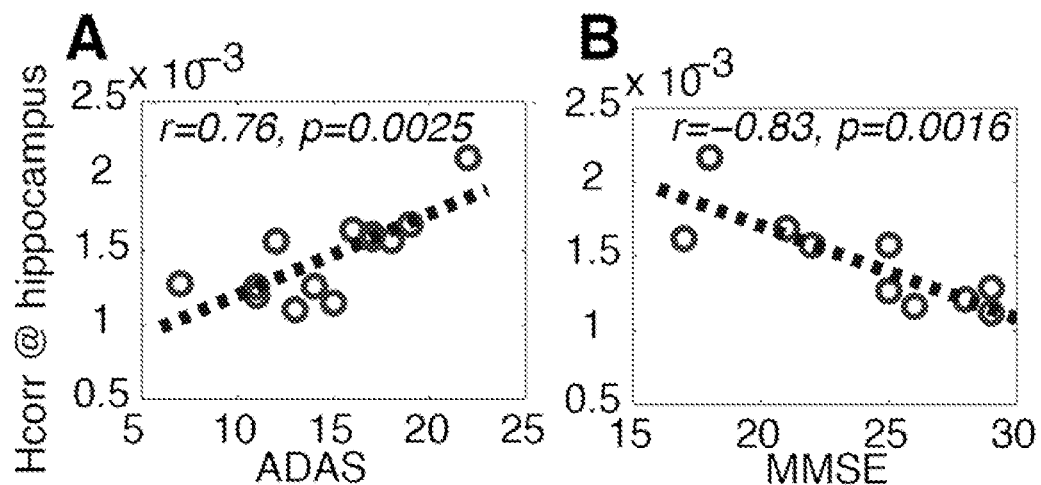
FIG. 2 shows that $H_{corr}$ at the hippocampus can predict the severity of disease (using the diagnostic ADAS-cog score (FIG. 1A) or the mini-mental state exam (MMSE) scores (FIG. 1B). Higher $H_{corr}$ correlates with a more advanced stage of disease, putatively due to increased synaptic dysfunction.

The present method indicates changes in $H_{corr}$ over the entire progression of the disease. At the earliest, asymptomatic stage, $H_{corr}$ shows an accelerated decrease as compared to that of controls, which indicates early cellular changes or cell death. At the symptomatic stages of the disease, however, elevated levels of $H_{corr}$ occur that parallel symptom severity. (See FIG. 2). It should be noted that, in healthy controls and asymptomatic individuals, a continuous decrease in $H_{corr}$ occurs with normal aging, but an accelerated decrease in asymptomatic individuals suggest an early sign of neurodegeneration. Stages of a neurodegenerative disease may be associated with a break-up of normally synchronized activity, detectable by changes in $H_{corr}$, due to synaptic dysfunction that progressively affects increasingly large parts of the brain. The methods include the combination of $H_{corr}$ values from different brain areas to more finely predict disease stages, given that neurodegenerative disorders have been shown to affect different brain areas as disease progresses.

Figure 4:
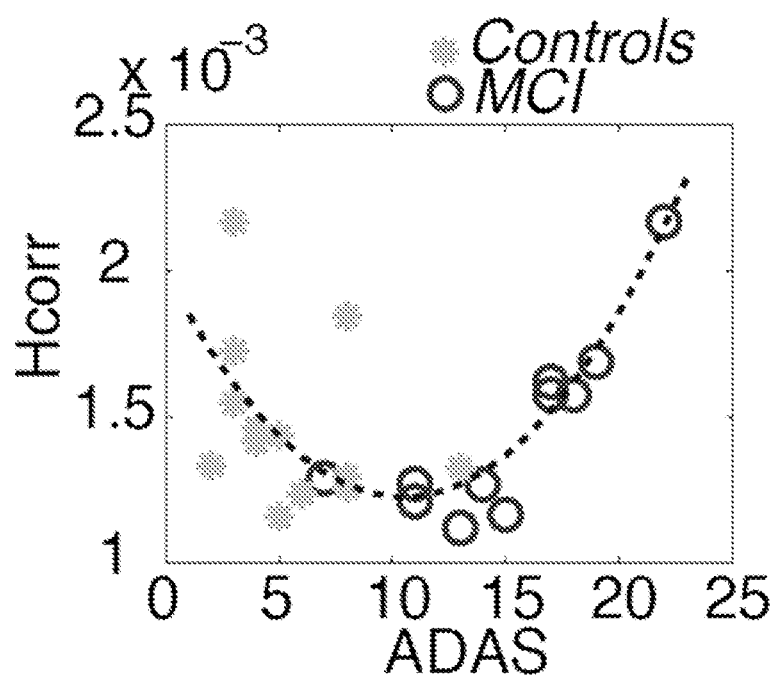
FIG. 4 shows that $H_{corr}$ has an initial decrease in asymptomatic individuals, putatively due to an initial loss of inhibitory synapses leading to more uniform activation patterns, followed by an increase, putatively due to increasing synaptic dysfunction that leads to a breakup of locally synchronized neuronal activity, for progressively affected individuals. Note that an ADAS score of 10 is the current cutoff for a clinical diagnosis of MCI.

To identify a person at or near the onset of clinical symptoms, it is necessary to disambiguate an increase either by (i) comparing a subsequent $H_{corr}$ to a subject's previous scan or scans (e.g., an increase in $H_{corr}$ after years of a steady decrease is a sign of significant disease progression), ii) comparing a subject's $H_{corr}$ to controls along with a neuropsychology assessment, like MMSE or ADAS-cog (e.g., an $H_{corr}$ in the "normal" range but with a ADAS-cog score near the cut-off score for MCI diagnosis indicates an onset of clinical symptoms, see FIG. 4).

The methods set forth herein can further comprise developing a normative standard for neural activity in a region of interest in response to an activation task or for responses obtained from the resting state, based on $H_{corr}$ values gathered from control subjects. The $H_{corr}$ of the subject can be compared to this normative standard in order to identify increases or decreases in $H_{corr}$. In addition, the methods can further comprise the combination of $H_{corr}$ values from different brain areas and possibly further indices such as neuropsychological test scores, and training a classification algorithm to combine these values to improve prediction accuracy relative to predictions based on $H_{corr}$ calculated from a single brain region.

During the fMRI, the subject may be asked to perform an activation task or may be at rest or essentially at rest (e.g., watching television or performing a simple motor task with minimal cognitive demands. There are advantages to performing the fMRI when the subject is at a resting state or essentially a resting state, as this places lower cognitive demands on the subject and permits the measurement of $H_{corr}$ also in cognitively impaired subjects. One of skill in the art can measure neuronal function at any brain region using a single fMRI data set, in order to obtain a pattern of $H_{corr}$ values that correspond to a particular disorder or stage of a disorder with a short fMRI scan (such as a 5 minute resting state scan).

As used throughout, the control can be an age and intelligence matched peer or group of peers or can be the subject in a control state (e.g., prior to or after the effect of treatment). It is within the skill in the art to select the appropriate control subject, control value, or control group.

Further provided are methods of treating a subject with an early, asymptomatic stage of a neurodegenerative disease or a subject with a symptomatic neurodegenerative disease comprising identifying a subject with an early, asymptomatic stage of a neurodegenerative disease or a symptomatic neurodegenerative disease using fMRI and $H_{corr}$ as taught herein and administering to the subject an effective amount of an agent that prevents or delays the onset of symptoms of the neurodegenerative disease or that reverses or reduces symptoms. Optionally, the method further comprises assessing the level of $H_{corr}$ after administering the agent to the subject and/or selecting a drug that changes or stabilizes $H_{corr}$ in the subject toward or near control values or stabilizes the $H_{corr}$ of the subject over time. The provided methods thus allow an ongoing assessment of treatment and the responsiveness of the subject to a selected treatment. The goal in treating a subject with the early, asymptomatic stage of the neurodegenerative disease is to slow the accelerated decrease in $H_{corr}$ over time or to increase the $H_{corr}$ level closer to or within control levels. The goal in treating a subject with a symptomatic neurodegenerative disease is to reduce or stabilize the subject's $H_{corr}$ toward or within control levels.

Also provided is a method of staging a neurodegenerative disease comprising selecting a subject with a neurodegenerative disease; placing the subject in an MRI machine; acquiring fMRI data from the subject, optionally, while the subject performs an activation task calculating a measure of local regional heterogeneity ($H_{corr}$); calculating a measure of local regional heterogeneity ($H_{corr}$) in one or more brain regions, wherein $H_{corr}$ is calculated using a computer readable medium including program instructions for calculating $H_{corr}$; comparing the $H_{corr}$ from the subject to a plurality of $H_{corr}$ values corresponding to subjects with different stages of the neurodegenerative; and staging the neurodegenerative disease in the subject by identifying one or differences between the $H_{corr}$ from the subject and the plurality of $H_{corr}$ values corresponding to subjects with different stages of the neurodegenerative disease.

A method of determining the effectiveness of a treatment for a neurodegenerative disease is also provided that includes the steps of selecting a subject with a neurodegenerative disease;
placing the subject in an MRI machine; acquiring fMRI data from the subject, optionally, while the subject performs an activation task; calculating a measure of local regional heterogeneity ($H_{corr}$) in one or more brain regions, wherein $H_{corr}$ is calculated using a computer readable medium including program instructions for calculating $H_{corr}$; and comparing the $H_{corr}$ as calculated to the $H_{corr}$ of the subject prior to administration of an agent. A change in the $H_{corr}$ after treatment toward a control $H_{corr}$ indicates the agent is effective in treating the neurodegenerative disease. No change in $H_{corr}$ or a modulation in $H_{corr}$ away from control values indicates the agent is ineffective in treating the neurodegenerative disease in the subject. Compared to behavioral testing, $H_{corr}$ offers an advantage by detecting neuronal dysfunction before the onset of behavioral symptoms, thus, allowing use for screening and developing agents to prevent or delay the onset of neurodegenerative conditions like AD or MCI and to test the effectiveness of the agent.

As used throughout, neurodegenerative diseases include disorders marked by a progressive loss of neuronal structure or function and include, by way of example, Mild Cognitive Impairment (MCI), Parkinson's Disease (PD), Alzheimer's Disease (AD), and Huntington's Disease, HIV-Associated Neurocognitive Disorder (HAND).

As utilized throughout, MCI is a brain function syndrome involving the onset and evolution of cognitive impairments beyond those expected based on the age and education of the individual, but which are not significant enough to interfere with their daily activities. MCI that primarily affects memory is known as "amnestic MCI." With amnestic MCI, a person may start to forget important information that he or she would previously have recalled easily, such as appointments, conversations or recent events. Amnestic MCI is frequently seen as a prodromal stage of AD. Studies suggest that these individuals tend to progress to probable AD at a rate of approximately 10% to 15% per year. MCI that affects thinking skills other than memory is known as "nonamnestic MCI." Thinking skills that may be affected by nonamnestic MCI include the ability to make sound decisions, judge the time or sequence of steps needed to complete a complex task, or visual perception.

As utilized throughout, AD is a type of dementia that causes problems with memory, thinking and behavior. Symptoms usually develop slowly and get worse over time, becoming severe enough to interfere with daily tasks. In its early stages, memory loss is mild, but with late-stage Alzheimer's, individuals lose the ability to carry on a conversation and respond to their environment. As set forth below, there are several stages of AD. Although there are symptoms associated with each stage, these stages can overlap.

For example, at Stage 1 of AD, the subject does not experience any memory problems and there is no evidence of symptoms of dementia.

At Stage 2 of AD, the subject may feel as if he or she is having memory lapses, for example, forgetting familiar words or the location of everyday objects. However, no symptoms of dementia can be detected during a medical examination or by friends, family or co-workers.

At Stage 3 of AD, there is mild cognitive decline characterized by noticeable problems, for example, coming up with the right word or name; trouble remembering names when introduced to new people; having noticeably greater difficulty performing tasks in a social or work setting; forgetting material that one has just read; losing or misplacing a valuable object; or increasing trouble with planning or organizing.

At Stage 4 of AD, there is moderate cognitive decline characterized by, for example, forgetfulness of recent events; impaired ability to perform challenging mental arithmetic; for example, counting backward from 100 by 7 s; greater difficulty performing complex tasks, such as planning dinner for guests, paying bills or managing finances; forgetfulness about one's own personal history or becoming moody or withdrawn, especially in socially or mentally challenging situations.

At Stage 5 of AD, there is moderately severe cognitive decline where gaps in memory and thinking are noticeable, and individuals begin to need help with day-to day activities. At this stage, those with Alzheimer's may be unable to recall their own address or telephone number or the high school or college from which they graduated. They may become confused about where they are or what day it is, or have trouble with less challenging mental arithmetic, such as counting backward from 40 by subtracting 4 s or from 20 by 2 s. They may need help choosing proper clothing for the season or the occasion; still remember significant details about themselves and their family; and still require no assistance with eating or using the toilet.

Stage 6 of AD is characterized by severe cognitive decline. Memory continues to worsen, personality changes may take place and individuals need extensive help with daily activities. At this stage, individuals may lose awareness of recent experiences as well as of their surroundings; remember their own name but have difficulty with their personal history; distinguish familiar and unfamiliar faces but have trouble remembering the name of a spouse or caregiver; need help dressing properly; and may, without supervision, make mistakes such as putting pajamas over daytime clothes or shoes on the wrong feet; experience major changes in sleep patterns; need help handling details of toileting (for example, flushing the toilet, wiping or disposing of tissue properly); have increasingly frequent trouble controlling their bladder or bowels; experience major personality and behavioral changes, including suspiciousness and delusions (such as believing that their caregiver is an impostor) or compulsive; repetitive behavior like hand-wringing or tissue shredding; or tend to wander or become lost.

At Stage 7, AD is characterized by very severe cognitive decline. In the final stage of this disease, individuals lose the ability to respond to their environment, to carry on a conversation and, eventually, to control movement. They may still say words or phrases. At this stage, individuals need help with much of their daily personal care, including eating or using the toilet. They may also lose the ability to smile, to sit without support and to hold their heads up. Reflexes often become abnormal, muscles grow rigid and swallowing is impaired.

As utilized throughout, HAND refers to a set of neurological problems related to thinking, memory, mood, and sometimes physical coordination and function that occurs in subjects that are HIV-positive. HAND can often be mild so that these symptoms are barely detectable and unnoticed by the person with the condition. In this form, it is called asymptomatic neurocognitive impairment (ANI). HAND can also cause mild-to-moderate symptoms, at which point it is referred to as mild neurocognitive disorder (MND). In its most severe form, people can progress to HIV-associated dementia (HAD). All of these, from the asymptomatic to the debilitating, are covered under the term HAND.

Depending on the nature of the neurodegenerative disorder, one of skill in the art may choose to analyze $H_{corr}$ in one or more selected brain regions of interest (functional or anatomical). For example, the hippocampus or frontal cortex may be assessed in subjects with MCI or AD, whereas the substantia nigra, striatum or other parts of the basal ganglia may be assessed in subjects with Huntington's Disease or PD. In addition, the methods can further comprise the combination of $H_{corr}$ values from different brain areas and possibly further indices such a neuropsychological test scores, and training a classification algorithm to combine these values to improve prediction accuracy relative to predictions based on $H_{corr}$ calculated from a single brain region.

By way of example, a subject in need of screening for MCI or AD can be, but is not limited to, a subject experiencing memory lapses or memory loss, a subject experiencing any of the symptoms associated with amnestic MCI or non-amnestic MCI, a subject experiencing any of the symptoms associated with one or more stages of AD, a subject with a familial history of MCI or AD, a subject over 65 years of age, or a subject with a genetic predisposition to MCI or AD (for example, a subject with mutations in Presenilin 1, Presenilin 2 or Amyloid beta (A4) precursor protein or a subject with APOe-4 genetic risk). In the case of Huntington's Disease and PD, the subject may be experiencing tremors or other motor symptoms or may have genetic mutations associated with PD or Huntington's Disease. However, the subject can be asymptomatic and be in need of screening because of one or more risk factors, such as age, family history, history of concussions, and/or genetic predisposition, for example.

As used throughout, the subject can be a vertebrate, more specifically a mammal, for example, a human. The term does not denote a particular age or sex. As used herein, patient or subject may be used interchangeably and can refer to a subject with a disease or disorder. The term patient or subject includes human and veterinary subjects.

As utilized throughout, functional magnetic resonance imaging (fMRI) is an MRI procedure that measures brain activity by detecting associated changes in blood flow. This technique relies on the fact that cerebral blood flow and neuronal activation are coupled. When an area of the brain is in use, blood flow to that region also increases. fMRI imaging can be applied in combination with one or more stimuli, for example, an activation task, that activates specific regions of the brain or by imaging during the "resting state" when there is neither a task nor stimuli presented to subjects (resting state fMRI scans). Local brain activity is then measured on the basis of local hemodynamic changes (changes in deoxyhemoglobin concentration, measured as blood oxygen level dependent signal, or BOLD signal) that occur in response to the various activation tasks or are due to spontaneous neural activations (resting state scan). Rapid T2*-sensitive imaging is performed during the performance of activation tasks and during rest periods. fMRI scans are collected and analyzed using techniques designed to extract signal intensity information from the time series collected. fMRI data analysis involves (i) fMRI signal intensity information over time is correlated with the time course of the activation tasks to allow identification and visualization of task-related brain activity in the regions of interest; (ii) comparisons may then be performed between the fMRI data for the images obtained during the stimulus task periods and during the rest periods; (iii) patterns of neural activity can be compared to activity observed in controls and with statistical norms for healthy individuals and for patients known to be afflicted with a cognitive disorder, for example, MCI, AD or HIV-associated neurocognitive disorder (HAND). However, it has been shown that these traditional fMRI data analysis techniques are not sensitive probes of changes in neuronal specificity due to disease-induced neurodegeneration (as in AD). Measurements and comparisons are performed using a computer readable medium including program instructions for measurements and comparisons and, optionally, including a database of control values of healthy subjects and/or subjects with, for example, AD, MCI, or HAND.

The methods set forth herein involve measuring neuronal specificity and function in a region of interest in the brain (e.g., the hippocampus) from fMRI scans. Once these fMRI data are acquired, a measure of local regional heterogeneity ($H_{corr}$) is calculated using a computer readable medium including program instructions for calculating $H_{corr}$. In order to calculate $H_{corr}$, raw time series data are obtained from the fMRI scan, wherein the raw time series data correspond to the region of interest. The data are normalized but not smoothed, followed by removal of the mean, any linear trends, and low frequency variations. The fMRI data from every timepoint are used in a pair-wise correlation analysis between responses in each voxel $Vox_i$, which results in a set of pairwise correlation coefficients (for n voxels), $r_{ij}$.

$$r_{ij} = corr(Vox_i, Vox_j), i,j \in 1 \ldots n$$

A measure of local heterogeneity, $H_{corr}$, as the standard error of the mean (SEM) or standard deviation (SD) of those correlation coefficients ($r_{ij}$, i<j, because $r_{ij}=r_{ji}$, and $r_{ii}=1$) is calculated using the following equation:

$$H_{corr} = \sqrt{\frac{\sum_{i=1}^{n-1} \sum_{j=i+1}^{n} (r_{ij} - u)^2}{N \times (N-1)}},$$

$$\text{where } N = \sum_{i=1}^{n-1} i, u = \frac{1}{N} \sum_{i=1}^{n-1} \sum_{j=i+1}^{n} r_{ij}$$

In the methods provided herein the computer readable medium includes program code executable by a processor of a computing device or system. The program code comprises instructions for retrieving fMRI data attributed to a region of interest in the brain of a subject, code comprising instructions for performing a pair-wise correlation analysis and code comprising instructions for calculating $H_{corr}$. The computer readable medium can further comprise code with instructions for identifying an increase or a decrease in $H_{corr}$ as compared to a control. Optionally, the computer readable medium can include program code with instructions for comparing the $H_{corr}$ value of the subject with a database of $H_{corr}$ values for healthy subjects, subjects with MCI, and/or subjects with AD and identifying differences between the $H_{corr}$ value of the subjects and the $H_{corr}$ values in the database.

As utilized throughout, fMRI scans are usually performed over the whole brain but can also be obtained from subregions of the brain. A unique advantage of the novel $H_{corr}$ technique is that, using a single fMRI data set, neuronal dysfunctions in any set of brain regions can be probed, such as the hippocampus, frontal cortex, temporal cortex, occipital cortex, prefrontal cortex, thalamus, cerebellum, brainstem, or functionally-defined brain regions like the fusiform face area (FFA), visual word form area (VWFA), or parahippocampal place area (PPA). One of skill in the art can measure neuronal function at any brain region using a single fMRI data set, in order to obtain a pattern of $H_{corr}$ values that correspond to a particular disorder or stage of a disorder with a short fMRI scan (such as a 5 minute resting state scan). This pattern can be compared to a pattern of $H_{corr}$ values that correspond to a control subject, in order to identify a subject with a cognitive disorder or at risk for a cognitive disorder.

As set forth above, an increase in $H_{corr}$ as compared to $H_{corr}$ from a control subject is indicative of a subject with symptomatic neurodegenerative disease. Depending on the amplitude of the increase, the increase in $H_{corr}$ can be indicative of MCI, mild AD or a later stage of AD. An increase in $H_{corr}$ can be due to substantial synaptic dysfunctions. Progressive synaptic loss associated with neurodegenerative disease progression leads to a breakup of synchronized neuronal activity. This manifests in an increased variability of voxel-wise correlations. Thus, higher values of $H_{corr}$ predict synaptic dysfunction and worsening of the disease. In contrast, at early, including prodromal disease stages, $H_{corr}$ values are predicted to be lower, as theses disease stages may be associated with a loss of neuronal selectivity that leads to more uniform neuronal activation patterns. The methods include the combination of $H_{corr}$ values from different brain areas to more finely predict disease stages, given that neurodegenerative disorders have been shown to affect different brain areas as disease progresses.

Early identification of neurodegenerative disease allows the application of therapeutics before substantial degeneration has occurred, so as to prevent or reduce the loss of cognitive ability or function and to delay or prevent structural damage and mitigating symptoms. $H_{corr}$ analysis of fMRI data can be performed subsequent to the onset of symptoms in order to monitor progression or treatment, if any, of the disease. Further, depending on the amplitude of the increase in $H_{corr}$ as compared to a control, one of skill in the art can predict if the disease will progress, and if so, how rapidly and to what extent.

As utilized throughout, a control subject can be a healthy subject, or a subject that is at low risk for MCI or AD. A subject at low risk for MCI or AD can be, for example, an asymptomatic subject that is less than 65 years old, a subject with no familial history of MCI or AD or a subject that does not have a genetic predisposition for MCI or AD. The control subject can also be the same subject for which $H_{corr}$ values were obtained at an earlier timepoint, for example, before the onset of AD or MCI. Any of the control subjects provided herein can also be an age-matched control.

The methods set forth herein can further comprise developing a normative standard for neural activity in a region of interest in response to an activation task or for responses obtained from the resting state, based on $H_{corr}$ values gathered from control subjects. The $H_{corr}$ of the subject can be compared to this normative standard in order to identify increases or decreases in $H_{corr}$. In addition, the methods can further comprise the combination of $H_{corr}$ values from different brain areas and possibly further indices such a neuropsychological test scores, and training a classification algorithm to combine these values to improve prediction accuracy relative to predictions based on $H_{corr}$ calculated from a single brain region.

The methods provided herein can be used in combination with other methods in order to identify a subject with a neurodegenerative disease or at risk of developing a symptomatic neurodegenerative disease. The methods provided herein can be combined with one or more of a physical examination, a neurological examination, a brief mental status test, neuropsychological testing to assess thinking and memory, an ADAS-cog score, a CT scan, a PET scan or a blood test that identifies biomarkers of MCI or AD. Similarly various neurological tests of motor function can also be used to diagnosis PD or Huntington's Disease or other neurodegenerative diseases.

In the treatment methods provided herein, the diagnostic methods can be combined with agents used to treat the neurodegenerative disease. Optionally, the agent can be selective, for example, for MCI or AD or a particular stage thereof and can be combined with a variety of other treatment methods (e.g., surgical stimulation). In the methods set forth herein to treat a stage of AD, the agent can be, but is not limited to, donepezil HCl)(ARICEPT® or memantine (NAMENDA®) (Merz Pharma GMBH & CO, Frankfurt, Germany)), galantamine (RAZADYNE® (Johnson & Johnson, New Brunswick, N.J.), rivastigmine tartrate (EXELON® (Novartis, Basel, Switzerland)). Known medications for treating a subject with HIV which can be used or combined with agents identified with screening methods taught herein include, without limitation, Highly Active Antiretroviral Therapy (HAART).

Methods herein can be used to determine the effectiveness of treatment. If the treatment is not effective, one of skill in the art can choose to change the dosage of the agent, administer a second agent, and/or administer a different agent. One of skill in the art could also choose to combine the agent with another agent, at the same or a different dose. If the treatment is effective, depending on the efficacy of the agent, one of skill in the art can choose to maintain the treatment or modify the treatment by changing the dosage, combining the agent with another agent or administering a different agent in order to further improve efficacy.

The effective amount of the agent or pharmaceutically acceptable salts thereof as described herein may be determined by one of ordinary skill in the art and includes exemplary dosage amounts for a mammal of from about 0.001 to about 50 mg/kg of body weight of active agent per day, which can be administered in a single dose or in the form of individual divided doses, such as from 1 to 4 times per day. The dosage ranges for administration are those large enough to produce the desired effect in which one or more symptoms of a cognitive disorder are affected. The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days, and may be continued indefinitely. Dose range should not exceed the maximally tolerated clinical dose, which can vary across compounds depending on potency, formulation, and duration of action. Effective doses can also be extrapolated from dose-response curves derived from in vitro or animal models.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1 Detection of Aging-Related Cognitive Decline (FIG. 1)

Three 6.5-minute runs of fMRI data were collected from ten healthy older adults (68.1±3.1 years old, seven women) while they were performing a motor task embedded with an implicit sequence. Verbal fluency and episodic memory performance was assessed 1 or 2 days later, using Controlled Oral Word Association Test-FAS and University of Southern California-Repeatable Episodic Memory Test, respectively. $H_{corr}$ was calculated for the following regions: hippocampus (a critical brain region for memory), and parahippocampus, and the visual word form area or VWFA (a critical brain region for language). For hippocampus and parahippocampus, respectively, the data from left and right hemisphere were collapsed together. Performance of episodic memory (total units) was quantitatively predicted by $H_{corr}$ (r=0.82, p<0.004, FIG. 1), but not by a conventional analysis (p>0.68) of fMRI responses in hippocampus. The results show that, in healthy older adults, $H_{corr}$ in individual brain region is correlated with performance of the corresponding cognitive functions, with a lower $H_{corr}$ value corresponding to a decrease in performance, likely due to age-related neuronal dedifferentiation.

Example 2 Detection of Mild Cognitive Impairment Eleven individuals with MCI (age 70.1±7.4, four female) and thirteen healthy controls (age 66.4±8.2, 7 female) participated in a clinical study on the drug Donepezil, which was prescribed to all participants during the 2-5 month study period. Cognitive function was assessed before and after the clinical drug period using AD Assessment Scale-Cognitive subscale (ADAS-Cog) and Mini-Mental Status Examination (MMSE), along with two fMRI scans to assess modulations in neuronal function. The fMRI study included three 11-minute runs. During the first run, subjects were instructed to judge whether a word on the screen referred to an animate or non-animate object. Then, during the 2nd and 3rd runs, subjects were instructed to judge whether a word on the screen had been shown to them during the first run or not. $H_{corr}$ in Hippocampus Predicts AD Severity in Individuals with MCI In individuals with MCI, ADAS scores were quantitatively predicted by $H_{corr}$ in the hippocampus (r=0.81, p<0.003, FIG. 2A; higher ADAS scores indicate higher degrees of impairment). The strong positive correlation (in contrast to the results from healthy elders on an episodic memory test) suggests that substantial and widespread synapse loss—which would result in a desynchronization of local neuronal activity—is already present in individuals with MCI. Similar results were observed with MMSE scores (r=−0.83, p<0.002, FIG. 2B; lower MMSE scores indicate higher degrees of impairment). These strong and robust correlation results show that $H_{corr}$ in the hippocampus can serve as a neurally-based measure of disease progression.

$H_{corr}$ is Highly Efficient in Examining Therapeutic Effects of AD Drugs

The effects of a drug (Donepezil) treatment were evaluated using $H_{corr}$ in the hippocampus, along with clinical assessments like MMSE and ADAS. A weak improvement (undetectable via MMSE (p>0.43 or ADAS, p>0.55) was revealed by a reduction in $H_{corr}$ at hippocampus (p=0.079).

Figure 3:
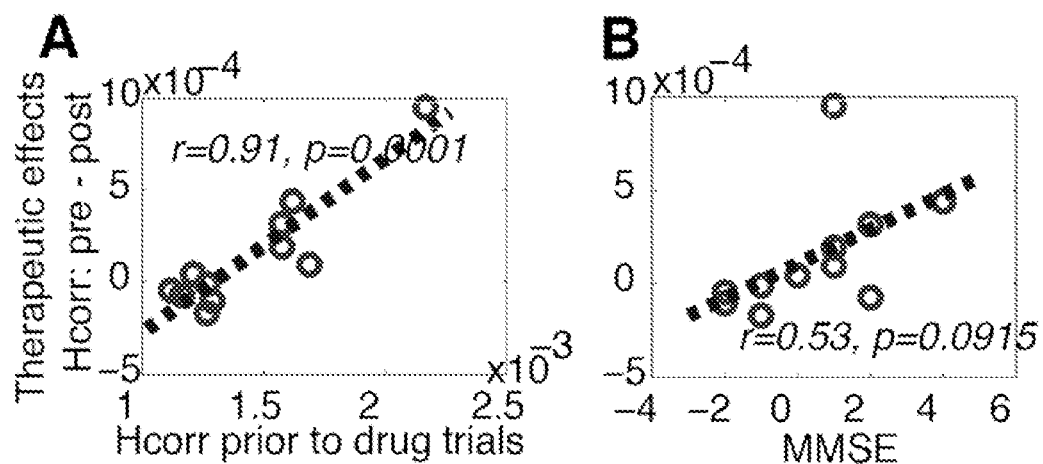
FIG. 3 shows that $H_{corr}$ can efficiently measure drug therapeutic effects. Using $H_{corr}$, it is clear that donepezil HCl (ARICEPT®, Eisai R & D Management Co., Tokyo, JP) is effective in subjects with a more advanced stage of AD (high $H_{corr}$, cf.

A close examination revealed that the drug Donepezil was more effective with patients at advanced stages of disease, but not with those at earlier stages of disease (r=0.91, p=0.0001, FIG. 3A). In the five patients at advanced stages of disease (original $H_{corr}$>0.0015), a small but significant improvement in MMSE (p<0.04) was also found, but not in the other six patients with an original $H_{corr}$ less than 0.0015 (p>0.32), in line with recent reports that Donepezil is more effective in treating individuals at more advanced stages of AD. Furthermore, a correlation analysis between the changes in MMSE and $H_{corr}$ revealed that patients with improvements at the neuronal level (measured as a reduction in $H_{corr}$) are more likely to have improvements at behavioral level (r=0.53, p=0.092, excluding one outlier subject (i.e., having a change in neuronal level but very limited improvements at behavioral level) yields a highly significant correlation, r=0.80, p=0.0056, FIG. 3B). The results show that $H_{corr}$ is highly sensitive to drug treatment, and might serve as a superior alternative to evaluate therapeutic effects than more commonly used behavior-based diagnoses, such as MMSE or ADAS, which are both shown to be less sensitive than $H_{corr}$. FIG. 3 shows that $H_{corr}$ can efficiently measure drug therapeutic effects. Using $H_{corr}$, it is clear that the drug ARICEPT® helps people at more advanced stage of AD, but not people at early stages of the disease. This fMRI technique can help drug companies move forward more rapidly, at reduced cost, to develop drugs for treating AD, as the (i) is highly sensitive in capturing neural therapy in the brain in vivo and (ii) can detect drug effects with a much smaller sample size. Furthermore, the $H_{corr}$ for a given individual can be used to monitor and adjust treatment for that individual.

$H_{corr}$ Predicts a U-Shaped Curve from Cognitive Normals to MCI Patients.

The bottom of the U-shape matches well with the clinical cutoff for MCI (ADAS>=10), suggesting a rebound in $H_{corr}$ could be an early indicator of MCI, prior to the onset of behavioral symptoms. See FIG. 4. If a person at risk goes through a routine MRI scan each year, an age-related slow decline is expected in $H_{corr}$ (see FIG. 4). A rapid decline in $H_{corr}$ followed by an increase in $H_{corr}$ indicates an increased likelihood that a subject will experience the onset of clinical symptoms of MCI. Since significant synapse damage can occur prior to the onset of MCI, treatment could be most effective during the period of decline in $H_{corr}$, and prior to the rebound (i.e., the subsequent increase in $H_{corr}$), particularly for individuals with one or more risk factors for MCI or AD.

Modulations in neuronal specificity were present in presymptomatic and prodromal patients, possibly due to synaptic toxicity caused by Aβ formations, and the presence and degree of synaptic dysfunction can be directly detected and quantified using the novel $H_{corr}$ technique. Usually, a lower $H_{corr}$ is associated with a lower behavioral performance as neurons in the region of interest (ROI) respond more similarly and are less able to differentiate inputs, and vice versa.

The computational simulations, confirmed by experimental data (see above), show that $H_{corr}$ first decreases with mild synapse loss (especially inhibitory ones), as a loss of intra-area inhibition leads to decreased differentiation of neuronal activation. However, as synapse loss progresses (extending to both excitatory and inhibitory synapses), $H_{corr}$ is predicted to increase as intra-area neuronal coupling breaks down, leading to a progressive disappearance of synchronized neuronal activation patterns in the region of interest. This predicts a U-shaped dependency of $H_{corr}$ as a function of disease progression and progressive decline in cognitive performance (see FIG. 4): $H_{corr}$ can quantitatively predict cognitive function in both healthy older adults, and individuals with mild cognitive impairment (MCI), but with the predicted opposite pattern, e.g., higher values of $H_{corr}$ in the hippocampus is associated with higher cognitive performance in healthy older adults, but lower cognitive performance in MCI patients (see FIG. 1, 2), with a clear transition.

Taken together, these data show a U-shaped change of $H_{corr}$ from cognitively normal to cognitively impaired during AD progression, as shown in FIG. 4. Fitting the data into a quadratic function revealed several notable findings: (i) The curve reached its minimum at an MMSE of 10, in line with the literature regarding the optimal cut-off score of ADAS-Cog in MCI diagnosis; ii) A rebound in $H_{corr}$ after aging-induced decrease would suggest significant pathological changes in hippocampus, thus the rebound has the potential to serve as a diagnostic biomarker to detect the onset of Alzheimer disease.

Figure 5:
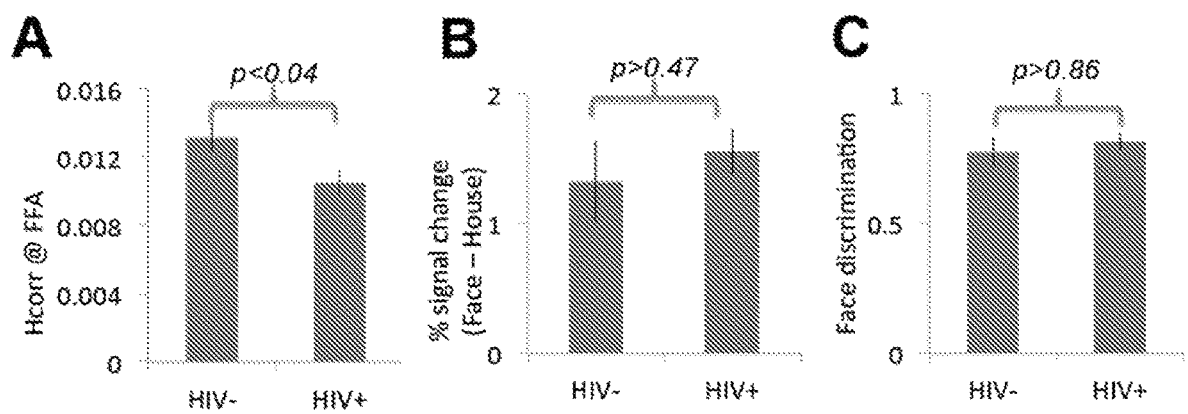
FIG. 5 shows that $H_{corr}$ decreases (p<0.04, FIG. 5A) were found in the right fusiform face area (FFA), a region of the right ventral cortex associated with face recognition, of HIV-positive women in the absence of behavioral deficits (p>0.46, FIG. 5C) or difference in conventional fMRI of the FFA (FIG. 5B).

Example 3 $H_{corr}$ is Highly Sensitive and can Detect Subtle Modulations in Neuronal Function in Asymptomatic HIV+ Patients Nineteen middle-aged women (12 HIV-positive, age 45-55 (49.9±3.5)) with normal behavior participated in a study to investigate the neural bases of HIV-associated neurocognitive disorders (HAND). See FIG. 5. A block design was used to collect MRI images from two localizer scans for each subject to identify FFA.

The FFA was first identified using the standard contrast of Face>House masked by Face>Baseline (p<0.0001, uncorrected) in each subject individually, with comparable size across subjects (45-48 voxels). Both the novel $H_{corr}$ and conventional data analyses were conducted on fMRI responses in the FFA. While conventional analysis found no differences between HIV-negative controls and HIV-positive patients (p>0.47, FIG. 5B), the novel $H_{corr}$ analysis revealed that $H_{corr}$ in the FFA was significantly lower in HIV-positive than HIV-negative participants (p<0.04, FIG. 5A), even in the absence of differences in face discrimination abilities (p>0.86, FIG. 5C) between the two groups. These results indicate that neuronal dysfunction is already present in middle-aged HIV-positive women, in the absence of measurable changes at the behavioral level, and that these modulations at the neuronal level can be detected by the novel $H_{corr}$ technique, but not conventional fMRI techniques, suggesting that $H_{corr}$ is highly sensitive and can detect early neuronal dysfunction in asymptomatic patients. Such a high sensitivity makes $H_{corr}$ a promising tool to evaluate drug or other therapeutic effects in asymptomatic patients, when behavioral assessments cannot detect differences.

Example 4: A Rebound in $H_{corr}$ with Disease Progression

Figure 6:
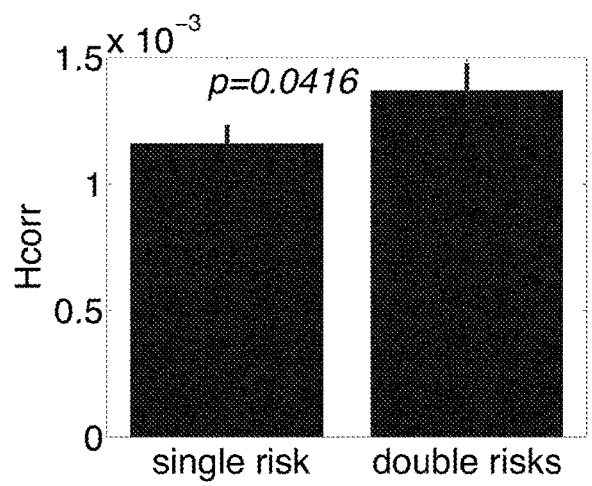
FIG. 6 shows $H_{corr}$ at the hippocampus in two sub-groups of the risk+ group, those with a single risk factor (genetic or family history), and those with double risk factors (genetic and family history). Error bars represent SEM.

As set forth above, while $H_{corr}$ at the hippocampus decreases prior to the onset of symptoms, it could also show signs of rebound prior to the onset of MCI. Interestingly, in subjects with normal cognitive performance, a clear rebound has been observed, when comparing individuals with a single risk factor (genetic or family history) to those with double risk factors (genetic and family history) (FIG. 6), suggesting the existence of significant pathological changes prior to the onset of MCI, especially in those at very high risk (genetic plus family history) of AD. Furthermore, these data also suggest that $H_{corr}$ can serve as an effective and non-invasive biomarker to evaluate those without behavioral symptoms, when treatment is likely to be most effective and when behavioral assays such as standard neuropsychology tests cannot detect treatment effects.

Example 5: A Reversed Correlation Between $H_{corr}$ and Cognitive Performance

Figure 7:
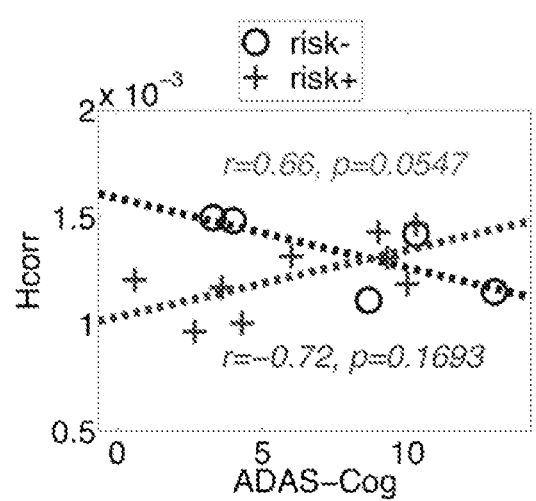
FIG. 7 shows a reversed correlation between $H_{corr}$ at the hippocampus and Cognitive Assessment (ADAS-Cog). In the risk− group, a higher $H_{corr}$ suggests better cognitive performance. By contrast, in the risk+ group, a higher $H_{corr}$ suggests lower performance.

As set forth above, while a higher $H_{corr}$ is correlated to better cognitive performance in healthy older adults, a higher $H_{corr}$ in individuals at more advanced stages of disease (i.e., MCI) is correlated with lower performance. Data from 14 subjects shows this correlation. It was also observed that a reverse correlation between $H_{corr}$ and cognitive performance is already present in healthy older adults at risk of AD (FIG. 7), suggesting that the rebound pattern happens much earlier, i.e., prior to the onset of MCI, probably due to significant synapse damage even in individuals without behavioral symptoms (see also, FIG. 6). As significant damage to synapses could occur at rather early stages of disease, i.e., prior to the onset of MCI, current treatments may be ineffective in fighting AD because of the late stage of use. Analysis of $H_{corr}$ could be used to focus treatment on asymptomatic individuals (prior to the onset of MCI).

What is claimed is:

1. A method of identifying a subject with an early, asymptomatic stage of a neurodegenerative disease comprising:
   a. selecting a subject in need of screening for the early, asymptomatic stage of a neurodegenerative disease;
   b. placing the subject in an MRI machine;
   c. acquiring fMRI data from the subject, while the subject performs an activation task or while the subject is in a resting state; and
   d. using the fMRI data acquired from the subject to calculate a measure of local regional heterogeneity of neuronal activation ($H_{corr}$) in one or more brain regions, wherein $H_{corr}$ is calculated using a computer readable medium including program instructions for calculating $H_{corr}$, and wherein a decrease in $H_{corr}$ as compared to $H_{corr}$ from a control subject is indicative of a subject with an early, asymptomatic stage of a neurodegenerative disease.

2. The method of claim 1, wherein the subject is at risk for mild cognitive impairment (MCI), Alzheimer's Disease (AD), or HIV-associated neurocognitive disorder.

3. The method of claim 1 wherein the region of interest is the hippocampus.

4. The method of claim 1 wherein the control is a healthy subject or a subject at low risk of developing MCI or AD.

5. The method of claim 1, further comprising repeating steps b-d one or more times to determine a rate of change in $H_{corr}$ in the subject, an accelerated rate of change as compared to a control indicating an early, asymptomatic stage of the neurodegenerative disease.

6. A method of treating a subject with an early, asymptomatic stage of a neurodegenerative disease comprising
   a. identifying a subject with an early, asymptomatic stage of a neurodegenerative disease according to the method of claim 1; and
   b. administering to the subject an effective amount of an agent that prevents or delays the onset of symptoms of the neurodegenerative disease.

7. The method of claim 6, further comprising assessing the level of $H_{corr}$ after administering the agent to the subject.

8. The method of claim 7, further comprising selecting a drug that increases $H_{corr}$ in the subject to or near control values.

9. A method of identifying a subject with a symptomatic neurodegenerative disease comprising:
   a. selecting a subject in need of screening for a symptomatic neurodegenerative disease;
   b. placing the subject in an MRI machine;
   c. acquiring fMRI data from the subject, while the subject performs an activation task or while the subject is in a resting state; and
   d. using the fMRI data acquired from the subject to calculate a measure of local regional heterogeneity of neuronal activation ($H_{corr}$) in one or more brain regions, wherein $H_{corr}$ is calculated using a computer readable medium including program instructions for calculating $H_{corr}$, and wherein an increase in $H_{corr}$ as compared to $H_{corr}$ from a control subject is indicative of a subject with a symptomatic neurodegenerative disease.

10. The method of claim 9, wherein the subject performs the activation task, wherein the activation task induces functional activity in a brain region of interest.

11. The method of claim 10, wherein the specific activation task is an episodic memory task.

12. The method of claim 9, wherein the subject has mild cognitive impairment (MCI), Alzheimer's Disease (AD), or HIV-associated neurocognitive disorder.

13. The method of claim 9, wherein the region of interest is the hippocampus.

14. The method of claim 9, wherein the control is a healthy subject or a subject at low risk of developing MCI or AD.

15. The method of claim 9, further comprising repeating steps b-d one or more times to determine a rate of change in $H_{corr}$ in the subject, an accelerated rate of change as compared to a control indicating progression of the neurodegenerative disease.

16. A method of treating a subject with a symptomatic neurodegenerative disease comprising
   a. identifying a subject with a symptomatic neurodegenerative disease according to the method of claim 9; and
   b. administering to the subject an effective amount of an agent that prevents or delays the onset of symptoms of the neurodegenerative disease.

17. The method of claim 16, wherein the agent is donepezil or nemantine.

18. A method of staging a neurodegenerative disease comprising:
   a. selecting a subject with a neurodegenerative disease;
   b. placing the subject in an MRI machine;
   c. acquiring fMRI data from the subject, while the subject performs an activation task or while the subject is in a resting state,
   d. using the fMRI data acquired from the subject to calculate a measure of local regional heterogeneity of neuronal activation ($H_{corr}$) in one or more brain regions, wherein $H_{corr}$ is calculated using a computer readable medium including program instructions for calculating $H_{corr}$;
   e. comparing the $H_{corr}$ from the subject to a plurality of $H_{corr}$ values corresponding to subjects with different stages of the neurodegenerative disease; and
   f. staging the neurodegenerative disease in the subject by identifying one or differences between the $H_{corr}$ from the subject and the plurality of $H_{corr}$ values corresponding to subjects with different stages of the neurodegenerative disease.

19. A method of determining the effectiveness of a treatment for a neurodegenerative disease comprising:
   a. selecting a subject with a neurodegenerative disease;
   b. placing the subject in an MRI machine;
   c. acquiring fMRI data from the subject, while the subject performs an activation task or while the subject is in a resting state; and
   d. using the fMRI data acquired from the subject to calculate a measure of local regional heterogeneity of neuronal activation ($H_{corr}$) in one or more brain regions, wherein $H_{corr}$ is calculated using a computer readable medium including program instructions for calculating $H_{corr}$; and
   e. comparing the $H_{corr}$ calculated in step (d) to the $H_{corr}$ of the subject prior to administration of the agent, wherein a change in the $H_{corr}$ after treatment toward a control $H_{corr}$ is effective in treating the neurodegenerative disease and wherein no change in $H_{corr}$ or a modulation in $H_{corr}$ away from control values is ineffective in treating the neurodegenerative disease in the subject.

20. The method of claim 19, wherein the neurodegenerative disease is MCI, AD, or HIV-associate neurocognitive disorder.

* * * * *